US011071650B2

(12) United States Patent
Iobbi

(10) Patent No.: US 11,071,650 B2
(45) Date of Patent: Jul. 27, 2021

(54) VISIBILITY ENHANCING EYEWEAR

(71) Applicant: Mario Iobbi, Basel (CH)

(72) Inventor: Mario Iobbi, Basel (CH)

( * ) Notice: Subject to any disclaimer, the term of this patent is extended or adjusted under 35 U.S.C. 154(b) by 0 days.

(21) Appl. No.: 16/622,173

(22) PCT Filed: Jun. 13, 2017

(86) PCT No.: PCT/US2017/037246
§ 371 (c)(1),
(2) Date: Dec. 12, 2019

(87) PCT Pub. No.: WO2018/231207
PCT Pub. Date: Dec. 20, 2018

(65) Prior Publication Data
US 2020/0121506 A1    Apr. 23, 2020

(51) Int. Cl.
*A61F 9/02* (2006.01)
*G06F 3/14* (2006.01)
*H04N 9/07* (2006.01)
*H04N 9/64* (2006.01)
*H04N 9/69* (2006.01)
*G06F 1/16* (2006.01)

(52) U.S. Cl.
CPC .............. *A61F 9/029* (2013.01); *G06F 3/14* (2013.01); *H04N 9/07* (2013.01); *H04N 9/646* (2013.01); *H04N 9/69* (2013.01); *G06F 1/163* (2013.01)

(58) Field of Classification Search
None
See application file for complete search history.

(56) References Cited

U.S. PATENT DOCUMENTS

| 6,549,231 B1 | 4/2003 | Matsui |
| 9,093,012 B2 | 7/2015 | Ma et al. |
| 9,097,891 B2 | 8/2015 | Border et al. |

(Continued)

FOREIGN PATENT DOCUMENTS

| DE | 20209101 U1 | 3/2003 |
| WO | 2011060525 A | 5/2011 |

OTHER PUBLICATIONS

P. Martinez Canada et al., "Embedded system for contrast enhancement in low-vision", Journal of Systems Architecture vol. 59, Jan. 2013, pp. 30-38.

(Continued)

*Primary Examiner* — James M Hannett
(74) *Attorney, Agent, or Firm* — Nicholson De Vos Webster & Elliott LLP

(57) ABSTRACT

An exemplary eyewear system includes a user interface and a composite lens. A first layer of the composite lens changes opacity in response to a signal. A second layer of the composite lens is a transparent display. The eyewear system further includes a camera, a processing device, and a memory. The processing device receives input via the user interface and, in response to the received input, sends a signal to the first layer of the composite lens to change the opacity of the first layer to cause the composite lens to be at least partially opaque, activates the camera, enhances video feed captured by the camera to increase the contrast of at least a portion of each of a plurality of frames of the video feed, and displays the enhanced video feed in real time using the second layer of the composite lens.

18 Claims, 4 Drawing Sheets

(56) References Cited

U.S. PATENT DOCUMENTS

| | | | | |
|---|---|---|---|---|
| 9,158,115 | B1* | 10/2015 | Worley | G02B 30/26 |
| 9,341,843 | B2 | 5/2016 | Border et al. | |
| 2005/0035980 | A1* | 2/2005 | Lonsing | G06T 15/00 |
| | | | | 345/633 |
| 2006/0262188 | A1* | 11/2006 | Elyada | G06T 7/97 |
| | | | | 348/143 |
| 2009/0246727 | A1* | 10/2009 | Vanini | G01J 3/52 |
| | | | | 433/26 |
| 2011/0258556 | A1* | 10/2011 | Kiciman | H04W 4/21 |
| | | | | 715/751 |
| 2012/0062444 | A1 | 3/2012 | Cok et al. | |
| 2012/0068913 | A1 | 3/2012 | Bar-Zeev et al. | |
| 2012/0235887 | A1 | 9/2012 | Border et al. | |
| 2012/0242865 | A1 | 9/2012 | Vartanian et al. | |
| 2013/0147686 | A1* | 6/2013 | Clavin | G06F 3/013 |
| | | | | 345/8 |
| 2016/0377864 | A1* | 12/2016 | Moran | G06F 3/011 |
| | | | | 345/8 |
| 2017/0038607 | A1* | 2/2017 | Camara | G02C 7/16 |
| 2017/0200296 | A1* | 7/2017 | Jones | G06F 40/58 |

OTHER PUBLICATIONS

Howard Moshtael et al., "High Tech Aids Low Vision: A Review of Image Processing for the Visually Impaired", TVST Translational Vision Science & Technology an ARVO journal, vol. 4, No. 4, Article 6, Aug. 14, 2015, 10 pages.

"Image Enhancement in Heavily Degraded Visual Environments using Image Processing Methods", SBIR-STTR America's Seed Fund, Department of Defense, Army, DoD 2017.1 SBIR Solicitation, A17-046, Release date Nov. 30, 2016, 2 pages.

Zhengzhou Li et al., "Image enhancement of high digital magnification for patients with central vision loss", SPIE-IS&T Electronic Imaging, Human Vision and Electronic Imaging XVI, SPIE vol. 7865, 2011, 8 pages.

"In Search of Better Visibility", Panasonic visibility enhancement technologies, White Paper, Copyright 2014 Panasonic System Networks Co., Ltd., 15 pages.

Raquel Urena et al., "Real-time bio-inspired contrast enhancement on GPU", Neurocomputing, Dec. 2013, 14 pages.

"Create The Next Level Drone Pilot Experience", Vuzix Blade, Augment Reality (AR) Smart Glasses for the Consumer, Copyright 2019 VUZIX, downloaded at https://www.vuzix.com/drones, on Dec. 4, 2019, 5 pages.

International Search Report and Written Opinion for International Application No. PCT/US2017/037246, dated Feb. 26, 2018, 12 pages.

Office Action, EP App. No. 17734191.4, dated Jan. 26, 2021, 4 pages.

* cited by examiner

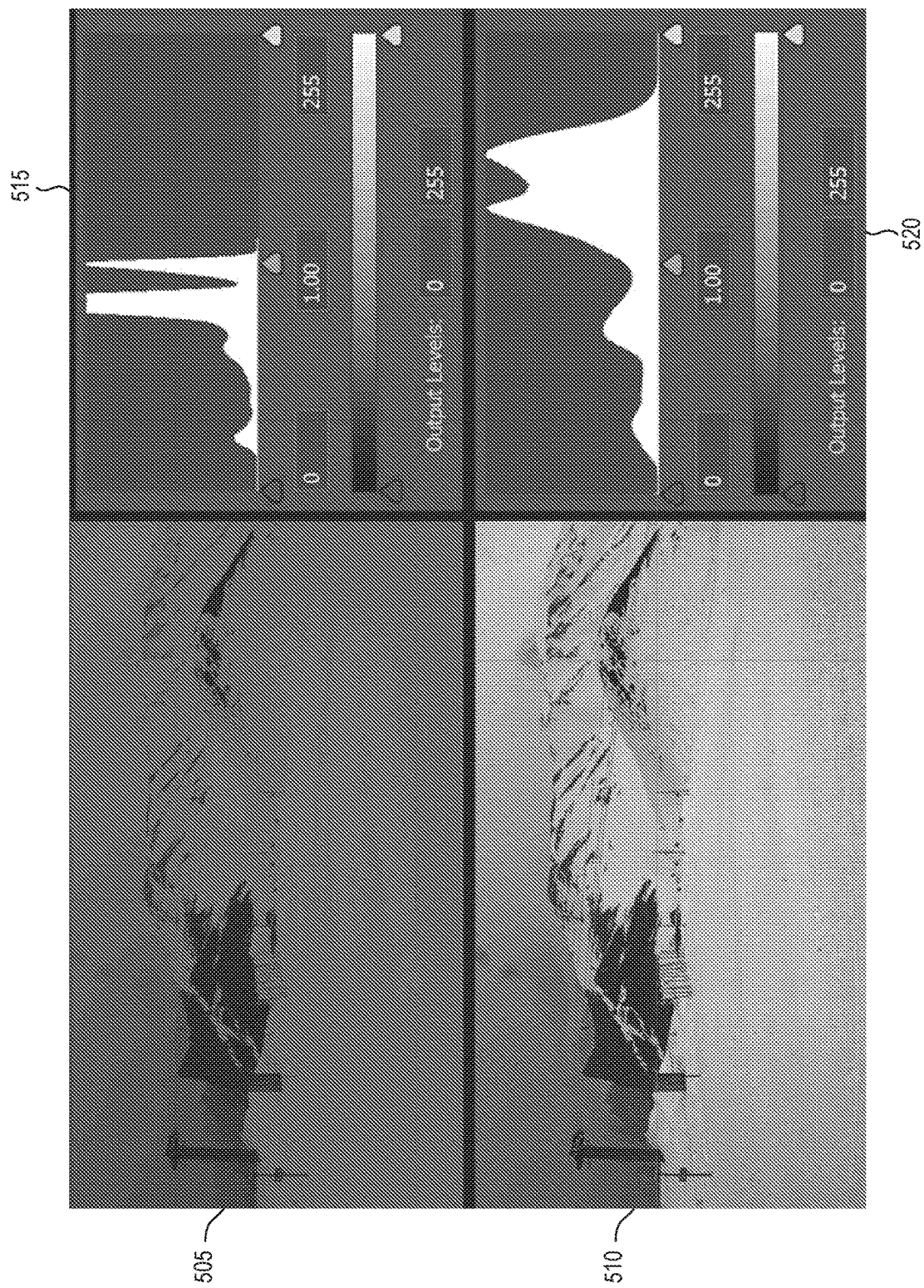

VISIBILITY ENHANCING EYEWEAR

CROSS-REFERENCE TO RELATED APPLICATIONS

This application is a national stage of International Application No. PCT/US17/37246, filed Jun. 13, 2017, which is hereby incorporated by reference.

FIELD OF THE INVENTION

The various embodiments described in this document relate to eyewear for outdoor activities to enhance visibility in variable and changing shadow, flat light, or white-out conditions.

BACKGROUND OF THE INVENTION

Poor visibility due to shadows, flat light, or white-out conditions increases risk during outdoor activities such as skiing, snowboarding, snowmobiling, and mountaineering. In situations with poor visibility conditions, it can be difficult to differentiate features to see and appreciate terrain, hazards, or obstacles. For example, during a white-out condition, moisture droplets suspended in the air refract light and obscure visibility. As a result, a skier in white-out conditions may become disoriented or lose sight of lift poles, trees, and other hazards.

BRIEF DESCRIPTION OF THE DRAWINGS

The present embodiments are illustrated by way of example and not limitation in the figures of the accompanying drawings, in which like references indicate similar elements, and in which:

FIG. 5 illustrates frames of an exemplary video feed and an exemplary enhanced video feed.

DETAILED DESCRIPTION

This document describes embodiments that relate to eyewear including a composite lens or screen that is transparent in a passive mode and at least partially opaque while in an active mode. In the active mode, one or more cameras capture image data in the user's field of view, a processor enhances the image data, and the processor outputs the enhanced image data for display on the interior of the at least partially opaque composite screen. As a result, embodiments provide the user with a better view of terrain, hazards, or obstacles in situations with poor visibility conditions. Because the eyewear is transparent in passive mode, it may be worn like traditional goggles and not need to be exchanged when the weather or lighting conditions change.

Figure 1:
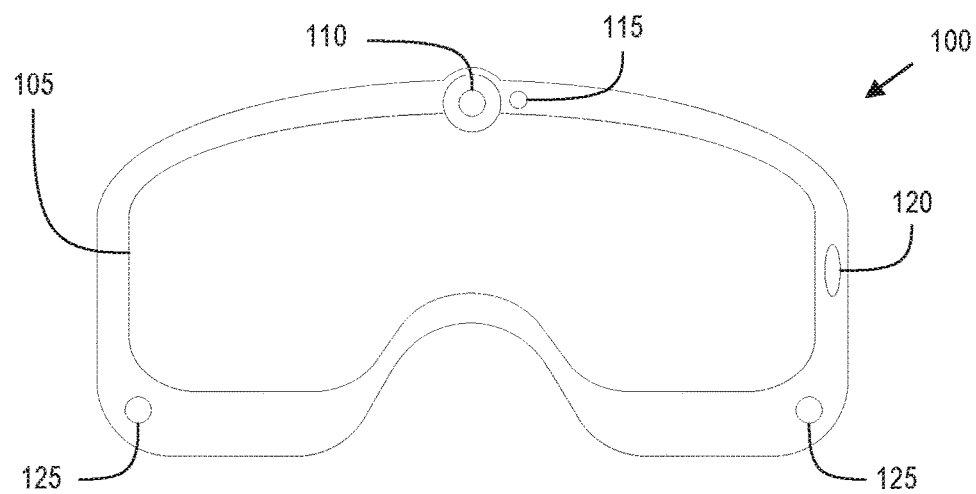
FIG. 1 illustrates an embodiment of visibility enhancing eyewear.

FIG. 1 illustrates an embodiment of visibility enhancing eyewear 100. Eyewear 100 illustrates an embodiment in the form of goggles, e.g., intended for snow sports. Alternate embodiments, however, include glasses, a mask, and/or helmet. For ease of description, however, this document collectively refers to such embodiments as eyewear.

Eyewear 100 includes composite lens 105. Composite lens 105 includes a plurality of layers. One of the layers of composite lens 105 transitions between a transparent state and an opaque state. Another layer of composite lens 105 displays processed/enhanced video feed and/or other image data. This document describes composite lens in greater detail with reference to FIG. 2.

Eyewear 100 further includes camera 110 mount in proximity to composite lens 105. While the drawing illustrates a single camera 110, embodiments may include multiple cameras 110. For example, such an embodiment may include two cameras 110 mounted within the body of eyewear 100 at a distance from center based upon a typical pupillary distance for adults (around 54-68 mm).

Camera(s) 110 have a viewing angle or field of view at least equivalent to a user's field of view of incoming visible light from the environment while the composite lens 105 is transparent. For example, the approximate field of view for human eyes (binocular visual field) is 100 degrees vertical and 200 degrees horizontal. This field of view may be partially obstructed or otherwise limited by the body or other components of eyewear 100 when worn. The angular extent of a scene imaged by camera(s) 110 is in the range of the unobstructed field of view for human eyes and that field of view as limited by the body or components of eyewear 100.

In one embodiment, one or multiple camera(s) 110 capture image data with a color depth greater than eight-bit color. For example, using more than eight bits to represent the color of each pixel increases the range of colors captured and provides eyewear 100 more visually apparent results in enhancing images via changes to contrast, white balance, tone, etc. The greater camera color resolution enables small variations in image data to be determined and enhanced during transformation while avoiding artefacts such as banding. This document describes transformation in greater detail with reference to FIGS. 4 and 5.

In one embodiment, multiple cameras 110 capture a three-dimensional video feed. For example, each of cameras 110 has a separate image sensor respectively capturing the scene in the field of view. In such an embodiment, eyewear 100 displays the three-dimensional video feed to a user, e.g., using dual displays or segregated display areas for each video feed, time-based multiplexing to combine video feeds, or side by side or top-bottom multiplexing to combine video feeds.

In one embodiment, eyewear 100 includes a camera 110 that captures light wavelengths outside of a spectrum of light visible to human eyes. For example, at least one camera 110 may capture light within the infrared spectrum or within the ultraviolet spectrum. During a white-out condition, moisture droplets suspended in the air refract light and obscure visibility. Infrared light is less susceptible to scatter by fog or mist and can provide enhanced visibility. Additionally, capturing light wavelengths outside of a spectrum of light visible to human eyes enables eyewear 100 to display scenes in low-light conditions.

Eyewear 100 optionally includes light source 115. For example, light source 115 may emit a pattern of light outside of the spectrum of light visible to human eyes—within the infrared spectrum or within the ultraviolet spectrum. In one embodiment, light source 115 is an infrared laser projector that emits a grid or other pattern of infrared light. Camera(s) 110 that capture light wavelengths in the infrared spectrum capture the pattern of infrared light, which eyewear 100 processes to enhance a video feed or otherwise help visualize surfaces to make terrain, hazards, obstacles, or other objects more visible to a user.

Eyewear 100 further includes one or more user interface elements 120. In one embodiment, interface element(s) 120 include a power button/input to activate and deactivate eyewear. Interface elements 120 may further include buttons/inputs to start or stop storage of video feed, start or stop display of information in addition to the video feed (e.g., time, location, messages, battery level, etc.), start or stop the recording of sound, etc.

Eyewear 100 optionally includes one or more microphones 125. Eyewear 100 uses microphone(s) 125 to receive audio input, e.g., to store with processed video feed, for an audio command to control a functionality of eyewear 100, etc.

As illustrated, eyewear 100 appears to be a single unit. Components of eyewear 100, however, may be separately connected/located and/or removable/detachable. Additionally, components may be placed, connected, or otherwise incorporated within the body of eyewear 100 in different locations than illustrated.

Figure 2:
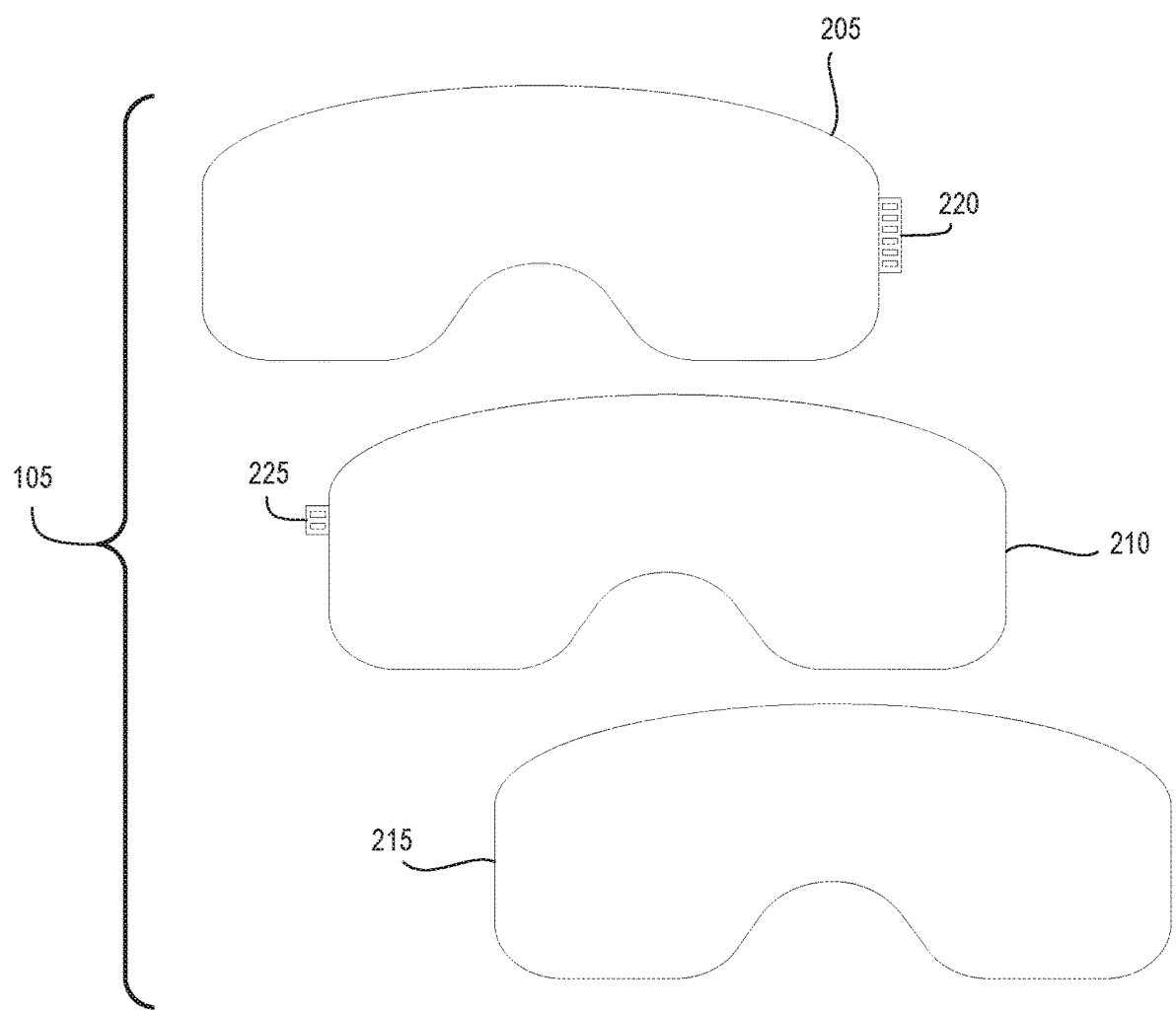
FIG. 2 illustrates exemplary layers of a composite lens for the visibility enhancing eyewear.

FIG. 2 illustrates exemplary layers of composite lens 105. As illustrated, composite lens 105 includes three layers. Layer 205 is a transparent display, layer 210 changes opacity in response to a voltage or other control signal, and layer 215 is a transparent screen or film. In some embodiments, composite lens 105 includes fewer or more layers than three. In one embodiment, each layer of composite lens 105 is an independent component that a user may separately remove or detach from eyewear 100. Alternatively, the layers of composite lens 105 make up a single component.

Layer 205 is an interior layer, e.g., of the three layers, in closest proximity to the eyes of the user when eyewear 100 is in use. In one embodiment, layer 205 is a transparent LED (light emitting diode), OLED (organic LED), and/or LCD (liquid crystal display) screen. For example, layer 205 may be a curved mirror or curved combiner transparent screen or a waveguide or light-guide-based transparent screen. Waveguide techniques for transparent screens include diffraction optics, holographic optics, polarized optics, reflective optics, and projection. Layer 205 is transparent when passive or otherwise not displaying a video feed. When active, portions of layer 205 may not be entirely transparent due to the display of a video feed.

In one embodiment, layer 205 provides a three-dimensional view. The three-dimensional view can allow user to appreciate distance or depth of field. For example, layer 205 may comprise dual displays or segregated display areas for each eye of the user. A separate video feed is presented upon each display/display area. Alternatively, layer 205 is a single display that presents three-dimensional views using time-based multiplexing or side by side or top-bottom multiplexing to combine video feeds.

Layer 205 includes connector 220. Connector 220 includes one or more pins for each of power, ground, positive lane(s), and/or negative lane(s). When coupled to eyewear 100 via connector 220, layer 205 receives a processed video feed to display to the internal side of composite lens 105.

Layer 210 is an intermediate layer within composite lens 105. In one embodiment, layer 210 is a smart glass and/or film to at least partially prevent incoming light from then environment that would interfere with the display of the processed video feed. Smart glass is glass or glazing alters light transmission properties of layer 210 in response to a voltage, light, heat, or another control signal. Layer 210 is opaque or partially opaque/translucent when active and transparent when passive. In good or adequate visibility conditions, the passive/transparent mode of layer 210 enables the user to see incoming visible light from the environment while layer 205 is passive/not displaying a video feed. In poor visibility conditions, the active mode of layer 210 obstructs light transmission, improving the visibility of video feed displayed on layer 205 and reducing visual imagery that is not a part of the video feed.

Layer 210 includes connector 225. Connector 225 includes one or more pins for each of power, ground, and/or control pins. When coupled to eyewear 100 via connector 225, layer 210 receives a signal (e.g., a voltage) to change opacity.

Layer 215 is an exterior layer. In one embodiment, layer 215 provides protection for other layers. For example, layer 215 may be a polarized or other lens/film through which a user can see incoming visible light from the environment while eyewear 100 is in a passive mode.

Figure 3:
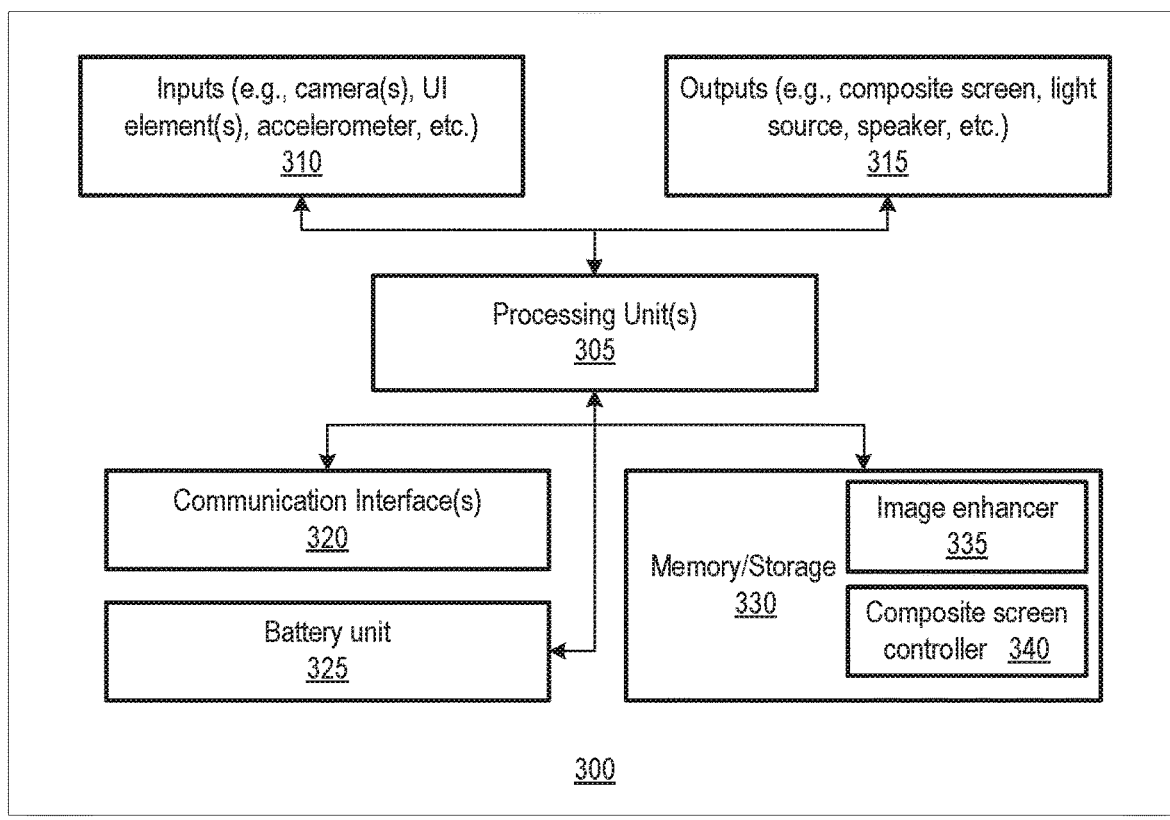
FIG. 3 illustrates, in block diagram form, components of the visibility enhancing eyewear.

FIG. 3 illustrates, in block diagram form, exemplary components 300 of eyewear 100. One or more buses interconnect components 300. Fewer or more buses than illustrated may interconnect components 300.

Components 300 include one or more processing units 305. Processing unit(s) 305 may include a central processing unit (CPU), microprocessor, microcontroller, system on a chip, or another integrated circuit.

Components 300 also include one or more device input components 310 and output components 315 coupled to processing unit(s) 305. Exemplary inputs 310 include camera(s) 110, user interface element(s) 120, microphone(s) 125, and/or an accelerometer. Exemplary outputs 315 include composite screen 105, light source 115, and/or speaker(s).

Components 300 also include one or more communication interfaces 320. For example, communication interface(s) 320 may include wired or wireless network interface controllers (NIC(s)) or other ports. Using communication interface(s) 320, eyewear 100 may communicate with an external device, such as computer or smartphone.

Components 300 also include battery unit 325. Battery unit 325 provides power to other components 300. In one embodiment, battery unit 325 is rechargeable. For example, communication interface 320 may further provide external power to recharge battery unit 325.

Components 300 also include memory/storage 330. Memory/storage 330 may include one or more of volatile and non-volatile memories, such as Random Access Memory (RAM), Read Only Memory (ROM), a solid-state disk (SSD), Flash, Phase Change Memory (PCM), or other types of data storage.

Memory/storage 330 may store data, metadata, and/or programs for execution by the processing unit(s) 305. For example, memory/storage 330 stores program modules such as image enhancer 335 and composite screen controller 340.

The functionalities of image enhancer 335 and composite screen controller 340, as well as other components 300, are described with reference to FIG. 4. While this document illustrates and describes embodiments implemented using software modules, alternate embodiments of the invention may be implemented in, but not limited to, hardware or firmware utilizing an FPGA, ASIC, and/or processing unit(s) 305. Modules and components of hardware or software implementations can be divided or combined without significantly altering embodiments of the invention.

Figure 4:
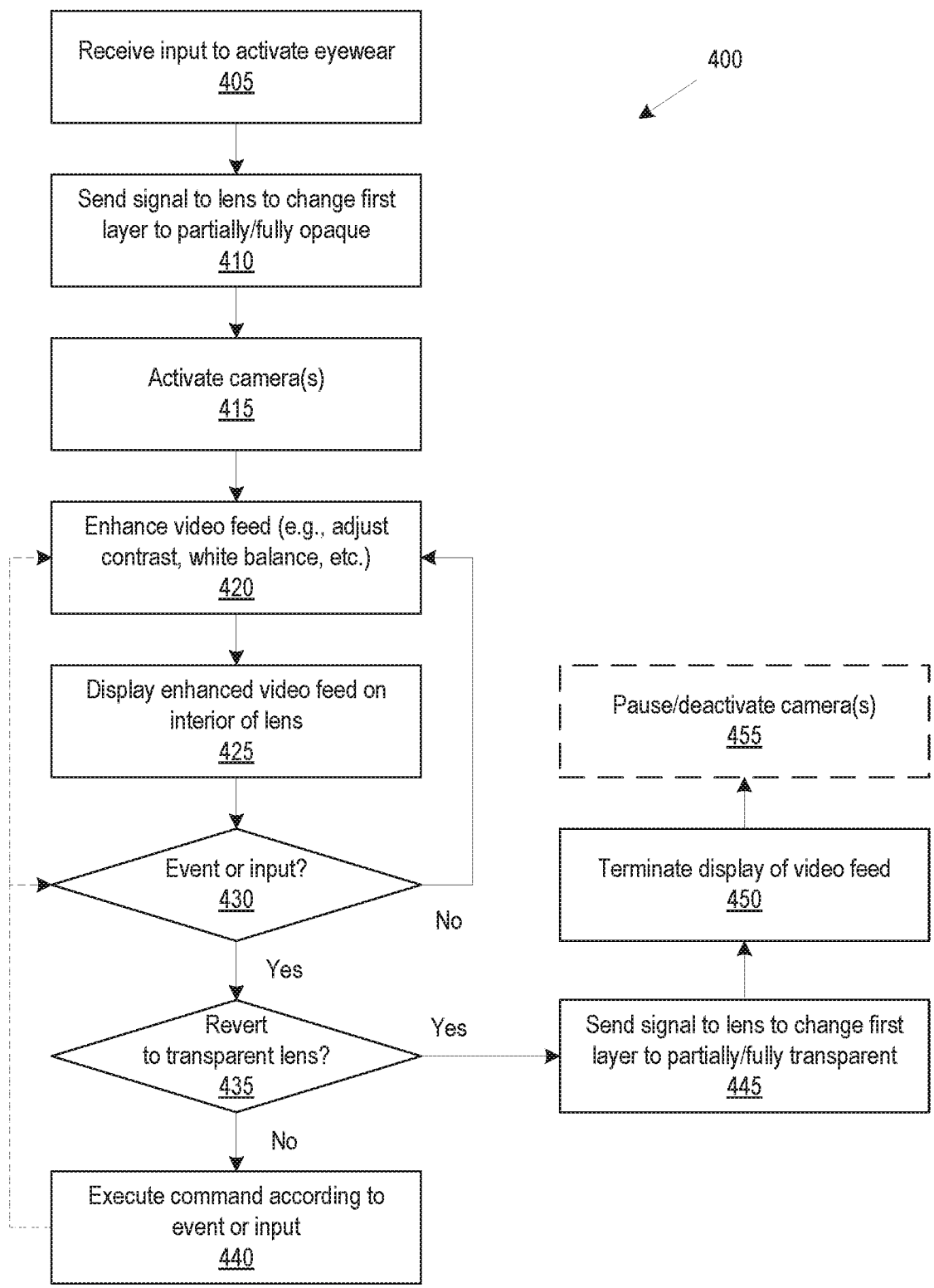
FIG. 4 is a flow chart illustrating an exemplary method of controlling the visibility enhancing eyewear.

FIG. 4 is a flow chart illustrating exemplary method 400 of controlling visibility enhancing eyewear 100. At block 405, processing unit 305 receives input to activate eyewear 100. For example, user interaction with user interface element 120 may cause processing unit to receive input to activate eyewear 100. In one embodiment, other such input may include a voice command received via microphone(s) 125, a gesture (e.g., of a hand) detected using camera(s) 110, and/or a wireless command (e.g., sent by a smartphone) received via communication interface 320.

At block 410, in response to the received input, processing unit 305 sends a signal to composite lens 105 to change the opacity of layer 210 from transparent to partially or fully opaque. For example, in an embodiment in which layer 210 is a smart glass, film, or glazing that alters light transmission properties of layer 210 in response to a voltage, light, heat, or another control signal, processing unit 305, executing composite screen controller 340, sends the corresponding control signal to change layer 210 from transparent to opaque, partially opaque, or translucent.

At block 415, further in response to the received input, processing unit 305 activates camera(s) 110. In one embodiment, activating camera(s) 110 includes powering on camera(s) 110 to generate video feed. In an alternate embodiment, camera(s) 110 are powered on prior to the received input and block 415 is omitted.

At block 420, further in response to the received input, processing unit 305 enhances or otherwise processes video feed captured by camera(s) 110. For example, processing unit 305, executing image enhancer 335, transforms frames of the video feed improve the visibility of objects, terrain, etc. that are difficult or impossible to view with an unaided eye. Processing unit 305 enhances the video feed using one or more parameters, such as: white balance, tone, light levels, shadow and/or highlight corrections, contrast, brightness, exposure, and/or merging separate video feeds. These parameters are examples. Processing unit 305 may also enhance video feed(s) using other parameters.

The white balance reflects the lighting conditions of the video feed(s). Adjusting the white balance can improve the ambient color of the video feed(s). In one embodiment, processing unit 305 processes the video feed using white balance to change the color temperature, causing the colors to appear cooler or warmer. In another embodiment, the parameter can change tint to compensate for or add color.

Some parameters are a subset of adjustments to tone. For example, contrast is the difference between darkest and lightest areas of frames in the video feed (i.e., range of tones). Adjusting contrast mainly affects the mid-tones. For example, enhancing or increasing the contrast in frames of the video feed can increase the visibility of objects in white-out conditions. Adjustments to light levels may also affect the range of tones. Highlights is another parameter example to change tone, which can adjust bright areas to darken features in an area of the frame that is otherwise "washed out." Similarly, shadows can adjust dark areas to brighten shadows and recover details that would otherwise be hidden by a lack of light. In one embodiment of adjusting tone, the transformation parameter can change the clipping of highlights and/or shadows. Adjustments to RGB curves can also affect highlights and shadows.

In one embodiment, processing unit 305 selects one or more parameters to enhance the video feed based upon user input. For example, the user input received at block 405, or other user input, may indicate visibility conditions. Processing unit 305 selects one set of one or more parameters for an input for white out conditions and another set of one or more parameters for an input for low light conditions. In another embodiment, processing unit 305 selects a default set of one or more parameters. In yet another embodiment, processing unit 305 analyzes the video feed to determine the visibility conditions and select the corresponding set of one or more parameters. For example, processing unit 305 may detect light levels, shadows, highlights, white levels, etc. in the video feed are above or below threshold value(s) and, in response, select one or more parameters to enhance the video feed accordingly.

In one embodiment, processing unit 305 optimizes the video feed prior to applying the selected parameters by determining which areas of the video feed frames to enhance. For example, processing unit 305 uses accelerometer input 310 to determine the orientation of the video feed by detecting the direction of the ground within the video feed. Processing unit 305 divides frames of the video feed into segments and determine segments likely to include images of the sky based upon location of the segments in the frames being in the opposite direction of the ground. Processing unit 305 omits those segments determined to likely to include images of the sky and enhances the remaining segments of the frames (e.g., the lower portion of the frames). Additionally or alternatively, processing unit 305 may detect which segments of frames that include obstacles, terrain, etc. or the sky using video feed from a camera 110 recording data outside of the visible spectrum and include/omit corresponding segments of frames of video feed from a camera 110 recording data within the visible spectrum. As a result of processing unit 305 reducing the amount of video feed to be enhanced, processing unit 305 conserves processing resources, such as processing time and power/battery life.

At block 425, further in response to the received input, processing unit 305 displays the enhanced video feed on the interior of composite lens 105 using layer 205. For example, changing layer 210 to an opaque/translucent state that reduces or blocks ambient light makes it easier for a user to view layer 205, the transparent display presenting the enhanced video feed. The display of enhanced video feed in real time on the full screen covering the user's entire field of view increases the likelihood of the user seeing obstacles, terrain, etc. that would otherwise be hidden by poor visibility conditions, e.g., as compared to a display screen that occupies only discrete portion of the user's field of view. Additionally, a display screen that occupies only discrete portion of the user's field of view may obstruct the user's line of sight.

The changing of layer 210 to an opaque/translucent state that reduces or blocks ambient light also provides the advantage of avoiding a need to align and/or overlay the display output together with the natural scene. The simultaneous viewing of both the natural scene and the modified or enhanced visual features introduces the disadvantage of incoming visible light from the environment interfering with the user's ability to view the display. Additionally, the registration of the display image to the natural scene requires additional processing resources and carries the risk of potential misalignment.

The display of the enhanced video feed in real time can be critical for user appreciation of depth of field and/or movement during some outdoor activities. In one embodiment, camera(s) 110 and/or display 210 have frame/refresh rate greater than 30 hertz to provide real time enhanced video feed. Additionally, in one embodiment, the processing latency to convert the received video feed to the enhanced video feed is less than 50 milliseconds. The frame/refresh rate and latency are important to avoid misleading artefacts. Similarly, it is important to prevent misleading display artifacts, e.g., due to limited color depth. As such, in one embodiment, camera(s) 110 and/or display 210 have color depth greater than 8 bit.

At block 430, processing unit 305 determines if it has detected an event or received an input to alter the operation of eyewear 100. For example, user input such as a detected hand gesture in the video feed, audio command detected via microphone(s) 125, or other user input received via user interface(s) 120 may trigger a change in operation. Additionally, processing unit 305 may detect battery power level falling below a threshold level, an interruption of video feed (e.g., due to a component failure), or the field of view of camera(s) 110 being at least partially obscured (e.g., due to snow, dirt, or another object covering at least a portion of the lens of camera(s) 110) as an event to trigger a change in operation. The detection of the field of view of camera(s) 110 being at least partially obscured may include, e.g., processing unit 305 determining that a threshold portion of one or more frames of video feed captured by one of camera(s) 110 represents the light captured is below a threshold level and/or as detected by a proximity sensor incorporated into camera(s) 110. In yet another embodiment, detecting an event includes processing unit 305 determining that at least a portion of the video feed has a contrast value above a threshold. For example, a contrast value above a threshold may indicate that an enhanced video feed will provide little benefit to the user and eyewear 100 can transition into a passive mode to save power. In one embodiment, processing unit 305 determines if the contrast value is above or below a threshold by evaluating tonal distribution in an image or frame, or portion thereof, within the video feed to determine if a threshold number of pixels in the image/frame represent each of different tonal values in the light grey to white tonal range. A larger representation of tonal values across this tonal range may indicate sufficient contrast while a smaller representation of values across this tonal range may indicate insufficient contrast. Tonal distribution is described further with reference to FIG. 5.

If processing unit 305 has not detected an event or received an input, method 400 continues to capture, process, and display video at blocks 420 and 425. If processing unit 305 detects an event or otherwise receives an input, at block 435, processing unit 305 determines if the event or input triggers reverting composite lens 105 back to a transparent state. Processing unit 305 reverts composite lens 105 back to a transparent state when the user no longer needs enhanced video for visibility, for power conservation, and/or for safety. For example, processing unit 305 may receive a detected gesture or other user input processing unit 305 interprets as a command to pause or stop use of camera(s) 110 and/or otherwise pause or stop the display of enhanced video feed on layer 205. The use of detected gesture(s) in the video feed reduces the need for user interface elements 120, such as buttons or touch screens, which may be difficult to operate during activities. As another example, detection of battery power falling below a threshold level may indicate that enhanced video feed will no longer have sufficient power to continue. An interruption of video feed (e.g., due to a component failure) or detection of the field of view of camera(s) 110 being at least partially obscured also are situations in which the enhanced video feed is no longer possible or useful. Maintaining layer 205 in a translucent, partially opaque, or opaque state can be frustrating or even hazardous to a user when the video feed has or will terminate. Returning layer 205 to a transparent state allows the user to continue to benefit from the passive use of eyewear 100, e.g., as one would use ordinary eyewear.

If the event or input does not trigger reverting composite lens 105 back to a transparent state, at block 440, processing unit 305 executes the command according to the event or input. For example, received inputs may trigger additional output displayed on layer 205. The additional output may include one or more information prompts, such as, location, speed, directions, altitude, map, telecommunication messages, etc. In one embodiment, received input may trigger the output of audio via one or more speakers 315. For example, eyewear 100 may wirelessly pair with a smartphone or other personal media device to playback music or other audio.

If the event or input triggers reverting composite lens 105 back to a transparent state, at block 445, processing unit 305, executing screen controller 340, sends a signal to composite lens 105 to change the opacity of layer 210 from partially or fully opaque to transparent. In one embodiment, sending the signal to composite lens 105 includes removing a voltage from layer 210 to revert layer 210 to a transparent state.

At block 450, processing unit 305 terminates the display of the video feed (if not already terminated by component failure) on the interior of composite lens 105, returning layer 205, and therefore composite lens 105, to a transparent state.

At block 455, processing unit 305 optionally pauses or deactivates camera(s) 110. For example, processing unit 305 pauses or deactivates camera(s) 110 to conserve power or in response to user input to do so. Alternatively, processing unit 305 continues to analyze video feed from one or both camera(s) 110 to detect, a gesture to activate the visibility enhancement functionality once again. In this alternate embodiment, such a gesture may be treated as input received in block 405 and block 415 may be omitted.

FIG. 5 illustrates exemplary video feed frame 505 and exemplary enhanced video frame 510. Video feed frame 505 represents video feed captured by camera 110 before any transformation to enhance visibility performed by processing unit 305. Video feed frame 510 represents the video feed after transformation to enhance visibility performed by processing unit 305. For example, during conditions with shadow, flat light, or white-out conditions the tonal values of pixels may have small variability to adequately for a user to visualize features and terrain. Histogram 515 is a visual representation of tonal distribution within video feed frame 505. The narrow distribution of color pixels in video feed frame 505 is, in particular, illustrated by the two tallest peaks within histogram 515 that represent little variation in lighter tonal values. As described above, the transformation performed by processing unit 305 enhances the video feed using one or more parameters, such as: white balance, tone, light levels, shadow and/or highlight corrections, contrast, brightness, exposure, and/or merging separate video feeds. For example, histogram 520 illustrates a greater distribution of tonal values as shown in the widening of the two peaks from histogram 515 to histogram 520. This increase in the distribution of tonal values results in enhanced visibility.

As evident from the description of embodiments in this document, a user of eyewear 100 can adapt the use of the active and passive modes of eyewear 100 to changing weather and visibility conditions without changing eyewear, while conserving battery power, and maintaining safety. Eyewear 100 can be worn passively (while composite lens 105 is transparent and no video output displayed) and only selectively display output when desired by user due to poor conditions. The power conservation in passive mode is a significant benefit for outdoor activities.

It will be apparent from this description that aspects of the inventions may be embodied, at least in part, in software. That is, computer-implemented method 400 may be carried out in one or more computer systems or other data processing systems, such as components 300 of eyewear 100, in response to its processor executing sequences of instructions contained in a memory or another non-transitory machine-readable storage medium. The software may further be transmitted or received over a wired or wireless connection via a network interface. In various embodiments, hardwired circuitry may be used in combination with the software instructions to implement the present embodiments. Thus, the techniques are not limited to any specific combination of hardware circuitry and software, or to any particular source for the instructions executed by a node and/or central controller. It will also be appreciated that additional components, not shown, may also be part of eyewear 100 and/or components 300, and, in certain embodiments, fewer components than that shown in FIGS. 1-3 may also be used in eyewear 100 and/or components 300.

In the foregoing specification, the invention(s) have been described with reference to specific exemplary embodiments thereof. Various embodiments and aspects of the invention(s) are described with reference to details discussed in this document, and the accompanying drawings illustrate the various embodiments. The description above and drawings are illustrative of the invention and are not to be construed as limiting the invention. References in the specification to "one embodiment," "an embodiment," "an exemplary embodiment," etc., indicate that the embodiment described may include a particular feature, structure, or characteristic, but not every embodiment may necessarily include the particular feature, structure, or characteristic. Moreover, such phrases are not necessarily referring to the same embodiment. Furthermore, when a particular feature, structure, or characteristic is described in connection with an embodiment, such feature, structure, or characteristic may be implemented in connection with other embodiments whether or not explicitly described. Additionally, as used in this document, the term "exemplary" refers to embodiments that serve as simply an example or illustration. The use of exemplary should not be construed as an indication of preferred examples. Blocks with dashed borders (e.g., large dashes, small dashes, dot-dash, dots) are used to illustrate virtualized resources or, in flow charts, optional operations that add additional features to embodiments of the invention. However, such notation should not be taken to mean that these are the only options or optional operations, and/or that blocks with solid borders are not optional in certain embodiments of the invention. Numerous specific details are described to provide a thorough understanding of various embodiments of the present invention. However, in certain instances, well-known or conventional details are not described in order to provide a concise discussion of embodiments of the present inventions.

Embodiments according to the invention are, in particular, disclosed in the claims directed to a method, a storage medium, and a system, wherein any feature mentioned in one claim category, e.g., the system, can be claimed in another claim category, e.g., the method, as well. The dependencies or references in the claims are chosen for formal reasons only. Any subject matter resulting from a deliberate reference back to any previous claims (in particular multiple dependencies) can be claimed as well, so that any combination of claims and the features thereof are disclosed and can be claimed regardless of the dependencies chosen in the attached claims. The subject-matter which can be claimed comprises not only the combinations of features as set out in the attached claims but also any other combination of features in the claims, wherein each feature mentioned in the claims can be combined with any other feature or combination of other features in the claims. Furthermore, any of the embodiments and features described or depicted herein can be claimed in a separate claim and/or in any combination with any embodiment or feature described or depicted herein or with any of the features of the attached claims.

It will be evident that various modifications may be made thereto without departing from the broader spirit and scope of the invention as set forth in the following claims. For example, the methods described in this document may be performed with fewer or more features/blocks or the features/blocks may be performed in differing orders. Additionally, the methods described in this document may be repeated or performed in parallel with one another or in parallel with different instances of the same or similar methods.

What is claimed is:

1. An eyewear system comprising:
   a user interface;
   a battery unit providing power to the eyewear system;
   a composite lens having first and second layers, wherein the first layer of the composite lens changes opacity in response to a signal to the first layer, and wherein the second layer of the composite lens is a transparent display;
   a first camera mounted in proximity to the composite lens;
   a processing device coupled to the composite lens and the first camera; and
   a memory coupled to the processing device, the memory storing instructions which, when executed by the processing device, cause the processing device to receive input via the user interface and, in response to the received input:
      send a signal to the first layer of the composite lens to change the opacity of the first layer to cause the composite lens to be at least partially opaque,
      activate the first camera to capture a video feed having a color depth that is greater than eight-bit color,
      enhance the video feed having a color depth that is greater than eight-bit color to increase contrast in at least a portion of each of a plurality of frames of the video feed,
      display, on an interior portion of the eyewear system, the enhanced video feed in real time using the second layer of the composite lens;
   wherein execution of the instructions further causes the processing device, in response to detecting one or more of (1) a power level of the battery unit has fallen below a threshold value, (2) the first camera is at least partially obscured, and/or (3) at least a portion of the video feed has a contrast value above a threshold, to:
      cause the first layer of the composite lens to change the opacity of the first layer from at least partially opaque to transparent, and
      terminate the display to the second layer of the composite lens.

2. The eyewear system of claim 1, further comprising:
   wherein execution of the instructions further causes the processing device, in response to detecting that a power level of the battery unit has fallen below a threshold value, to:
      deactivate the first camera.

3. The eyewear system of claim 1, wherein execution of the instructions further causes the processing device to determine that the first camera is at least partially obscured and, in response to the determination:
   deactivate the first camera.

4. The eyewear system of claim 1, wherein enhancing the video feed further comprises altering at least a portion of each of the plurality of frames of video feed using one or more of: white balance, tone, light levels, shadow and/or highlight corrections, and brightness.

5. The eyewear system of claim 1, further comprising a second camera mounted in proximity to the composite lens, wherein enhancing the video feed further comprises merging video feed from the first and second cameras.

6. The eyewear system of claim 5, wherein the first and/or second camera captures light wavelengths outside of a spectrum of light visible to human eyes.

7. The eyewear system of claim 6, further comprising a light source that emits a pattern of light outside of the spectrum of light visible to human eyes, the pattern emitted in a field of view captured by the first or second camera.

8. The eyewear system of claim 1, further comprising data storage, wherein the processing device stores the enhanced video feed.

9. The eyewear system of claim 1, wherein execution of the instructions further causes the processing device to:
  detect a gesture in the video feed; and
  in response to the detected gesture, performing one or more of:
    pausing of the first camera and/or display,
    resuming of the first camera and/or display, and
    storing the enhanced video feed.

10. The eyewear system of claim 1, wherein execution of the instructions further causes the processing device to select the portion of each of a plurality of frames of the video feed to enhance by increasing the contrast, the selection comprising:
  dividing the video feed into a plurality of segments;
  determining an orientation of the video feed with respect to the ground; and
  selecting one or more of the plurality of segments in a lower portion of the video feed with respect to the ground based upon the determined orientation.

11. A non-transitory computer-readable medium storing instructions, which when executed by a processing device, cause the processing device to perform a method of controlling an eyewear system including a user interface, a composite lens having first and second layers, wherein the first layer of the composite lens changes opacity in response to a signal to the first layer, and wherein the second layer of the composite lens is a transparent display, and a first camera mounted in proximity to the composite lens, the method comprising:
  receiving input via the user interface;
  in response to the received input:
    sending a signal to the first layer of the composite lens to change the opacity of the first layer to cause the composite lens to be at least partially opaque,
    activating the first camera to capture a video feed having a color depth that is greater than eight-bit color,
    enhancing the video feed having a color depth that is greater than eight-bit color to increase contrast in at least a portion of each of a plurality of frames of the video feed, and
    displaying, on an interior portion of the eyewear system, the enhanced video feed in real time using the second layer of the composite lens; and
  in response to detecting one or more of (1) a power level of the battery unit has fallen below a threshold value, (2) the first camera is at least partially obscured, and/or (3) at least a portion of the video feed has a contrast value above a threshold:
    causing the first layer of the composite lens to change the opacity of the first layer from at least partially opaque to transparent, and
    terminating the display to the second layer of the composite lens.

12. The non-transitory computer-readable medium of claim 11, the method further comprising:
  in response to detecting that a power level of a battery unit has fallen below a threshold value or that the first camera is at least partially obscured:
  deactivating the first camera.

13. The non-transitory computer-readable medium of claim 11, wherein enhancing the video feed further comprises altering at least a portion of each of the plurality of frames of video feed using one or more of: white balance, tone, light levels, shadow and/or highlight corrections, and brightness.

14. The non-transitory computer-readable medium of claim 11, wherein the eyewear system includes a second camera mounted in proximity to the composite lens, and wherein enhancing the video feed further comprises merging video feed from the first and second cameras.

15. The non-transitory computer-readable medium of claim 14, wherein the first and/or second camera captures light wavelengths outside of a spectrum of light visible to human eyes.

16. The non-transitory computer-readable medium of claim 15, wherein the eyewear system includes a light source that emits a pattern of light outside of the spectrum of light visible to human eyes, and wherein capturing light wavelengths outside of the spectrum of light visible to human eyes includes capturing the pattern emitted by the light source.

17. The non-transitory computer-readable medium of claim 11, the method further comprising:
  detecting a gesture in the video feed; and
  in response to the detected gesture, performing one or more of:
    pausing of the first camera and/or display,
    resuming of the first camera and/or display, and
    storing the enhanced video feed.

18. The non-transitory computer-readable medium of claim 11, the method further comprising:
  selecting the portion of each of a plurality of frames of the video feed to enhance by increasing the contrast, the selection comprising:
  dividing the video feed into a plurality of segments;
  determining an orientation of the video feed with respect to the ground; and
  selecting one or more of the plurality of segments in a lower portion of the video feed with respect to the ground based upon the determined orientation.

* * * * *